United States Patent
Park et al.

(10) Patent No.: US 10,304,637 B2
(45) Date of Patent: May 28, 2019

(54) ELECTRODE COMPRISING ORGANIC SEMICONDUCTOR MATERIAL, METHOD FOR MANUFACTURING ELECTRODE, AND SUPERCAPACITOR COMPRISING ELECTRODE

(71) Applicant: UNIVERSITY-INDUSTRY COOPERATION GROUP OF KYUNG HEE UNIVERSITY, Yongin-si (KR)

(72) Inventors: JongWook Park, Seoul (KR); Beomsoo Michael Park, Palatine, IL (US); Seungho Kim, Bucheon-si (KR)

(73) Assignee: UNIVERSITY-INDUSTRY COOPERATION GROUP OF KYUNG HEE UNIVERSITY, Yongin-Si (KR)

(*) Notice: Subject to any disclaimer, the term of this patent is extended or adjusted under 35 U.S.C. 154(b) by 197 days.

(21) Appl. No.: 15/509,942

(22) PCT Filed: Jan. 14, 2015

(86) PCT No.: PCT/KR2015/000392
§ 371 (c)(1),
(2) Date: Jul. 19, 2017

(87) PCT Pub. No.: WO2016/047868
PCT Pub. Date: Mar. 31, 2016

(65) Prior Publication Data
US 2017/0330698 A1    Nov. 16, 2017

(30) Foreign Application Priority Data
Sep. 23, 2014 (KR) .................. 10-2014-0126833

(51) Int. Cl.
*H01G 11/38* (2013.01)
*H01G 11/32* (2013.01)
(Continued)

(52) U.S. Cl.
CPC .............. *H01G 11/38* (2013.01); *B05D 1/40* (2013.01); *B05D 3/0254* (2013.01); *C07C 15/60* (2013.01);
(Continued)

(58) Field of Classification Search
CPC ........ H01G 11/38; H01G 11/28; H01G 11/46; H01G 11/48; H01G 11/62; H01G 11/36;
(Continued)

(56) References Cited

U.S. PATENT DOCUMENTS 5,172,307 A * 12/1992 Tabuchi ................ H01G 9/155
                                                                 29/25.03
5,369,546 A * 11/1994 Saito .................... H01G 9/155
                                                                 29/25.03
(Continued)

FOREIGN PATENT DOCUMENTS

JP          11-008165          1/1999
JP          11-238653          8/1999
(Continued)

*Primary Examiner* — David M Sinclair
(74) *Attorney, Agent, or Firm* — Lex IP Meister, PLLC

(57) ABSTRACT

The present invention relates to: an electrode comprising a current collector and a film located on the current collector, wherein the film comprises an organic semiconductor material and one selected from a carbon material, a metal oxide and a conductive polymer; a method for manufacturing the electrode; and a supercapacitor comprising the electrode.

29 Claims, 30 Drawing Sheets

(51) Int. Cl.

| | | |
|---|---|---|
| *H01G 11/68* | (2013.01) | |
| *H01G 11/86* | (2013.01) | |
| *C08K 3/04* | (2006.01) | |
| *B05D 1/40* | (2006.01) | |
| *B05D 3/02* | (2006.01) | |
| *C09D 5/24* | (2006.01) | |
| *C09D 125/02* | (2006.01) | |
| *C09K 11/06* | (2006.01) | |
| *H01G 11/28* | (2013.01) | |
| *H01G 11/36* | (2013.01) | |
| *H01G 11/46* | (2013.01) | |
| *H01G 11/48* | (2013.01) | |
| *H01G 11/62* | (2013.01) | |
| *C08F 12/32* | (2006.01) | |
| *C07C 15/60* | (2006.01) | |
| *H01G 11/52* | (2013.01) | |

(52) U.S. Cl.
CPC ............... *C08F 12/32* (2013.01); *C08K 3/04* (2013.01); *C08K 3/041* (2017.05); *C09D 5/24* (2013.01); *C09D 125/02* (2013.01); *C09K 11/06* (2013.01); *H01G 11/28* (2013.01); *H01G 11/32* (2013.01); *H01G 11/36* (2013.01); *H01G 11/46* (2013.01); *H01G 11/48* (2013.01); *H01G 11/62* (2013.01); *H01G 11/68* (2013.01); *H01G 11/86* (2013.01); *C08K 2201/001* (2013.01); *C08K 2201/011* (2013.01); *C09K 2211/1416* (2013.01); *C09K 2211/1425* (2013.01); *H01G 11/52* (2013.01); *Y02E 60/13* (2013.01)

(58) Field of Classification Search
CPC ........ H01G 11/68; H01G 11/86; H01G 11/32; C09D 5/24; C09K 11/06
See application file for complete search history.

(56) References Cited

U.S. PATENT DOCUMENTS

| | | | | |
|---|---|---|---|---|
| 5,744,258 | A | * 4/1998 | Bai | ............... H01M 4/04 |
| | | | | 429/209 |
| 2001/0053059 | A1 | * 12/2001 | Saito | ............... H01G 9/08 |
| | | | | 361/502 |
| 2002/0110729 | A1 | * 8/2002 | Hozumi | ............... H01G 4/32 |
| | | | | 429/130 |
| 2003/0068550 | A1 | * 4/2003 | Naoi | ............... H01G 11/42 |
| | | | | 429/213 |
| 2006/0039099 | A1 | * 2/2006 | Oizumi | ............... H01G 9/155 |
| | | | | 361/502 |
| 2009/0034158 | A1 | * 2/2009 | Sasaki | ............... H01G 9/058 |
| | | | | 361/502 |
| 2009/0122469 | A1 | * 5/2009 | Hatori | ............... H01G 9/058 |
| | | | | 361/525 |
| 2010/0142121 | A1 | * 6/2010 | Fujii | ............... H01M 4/587 |
| | | | | 361/502 |
| 2011/0236755 | A1 | * 9/2011 | Ogino | ............... H01G 11/28 |
| | | | | 429/218.1 |

FOREIGN PATENT DOCUMENTS

| | | |
|---|---|---|
| JP | 2002173371 | 6/2002 |
| JP | 2007273797 | 10/2007 |
| KR | 10-1161721 | 7/2012 |
| KR | 20130085548 | 7/2013 |
| KR | 20140111181 | 9/2014 |

* cited by examiner

ELECTRODE COMPRISING ORGANIC SEMICONDUCTOR MATERIAL, METHOD FOR MANUFACTURING ELECTRODE, AND SUPERCAPACITOR COMPRISING ELECTRODE

BACKGROUND OF THE INVENTION (a) Field of the Invention

An electrode including an organic semiconductor material, a method for manufacturing an electrode, and a supercapacitor including the electrode are disclosed.

The present invention is derived from research conducted as a strategic core material technology development project by the Ministry of Trade, Industry and Energy and the Korea Institute for Industry/Technology Assessment and Management (Project No.: M-2013-A0158-00009, Title: Charge transporting material technology for solution process for high efficiency energy part) and as a senior researcher support project by the Ministry of Education, Science and Technology and the National Research Foundation of Korea (Project No.: 2012001846, Title: Research on a future π electronic material system using molecule precision control fusion technique.

(b) Description of the Related Art

As interest in the environment and energy is increased, research on an energy storage system such as a lithium rechargeable battery, a capacitor, and the like is actively being made. In particular, a supercapacitor and a lithium rechargeable battery applicable in a field requiring high-capacity and high power characteristics have recently drawn the most attention.

In general, a capacitor stores electricity by using capacitance produced by applying a voltage between two electrodes in an electrolyte. A supercapacitor has higher capacitance than a general capacitor and is also referred to as an ultracapacitor.

The supercapacitor is classified into an electric double layer capacitor, a pesudo capacitor, and a hybrid capacitor depending on a material used for an electrode. The electric double layer capacitor uses an electric double layer charge layer, and the pesudo capacitor is a capacitor enlarging capacitance through an oxidation reduction reaction. The hybrid capacitor consists of a mixing electrode of the electric double layer and the pesudo capacitor.

The supercapacitor stores energy by using an electrochemical mechanism generated due to adsorption of electrolyte ions in the surface of an electrode. Accordingly, the supercapacitor has a high output and may maintain initial performance despite tens of thousands of charges and discharges.

This energy storage system uses various electrode materials such as a carbon material, a metal oxide, a conductive polymer, and the like. In particular, research on applying a composite electrode material obtained by mixing two or more selected from the electrode materials is actively made.

SUMMARY OF THE INVENTION

Technical Object

An electrode having large specific capacitance and excellent charge and discharge characteristics by including an organic semiconductor material, a method of manufacturing the electrode and a supercapacitor including the electrode are provided.

Technical Solution

An embodiment of the present invention provides an electrode including a current collector and a film located on the current collector, wherein the film includes at least one selected from a carbon material, a metal oxide, and a conductive polymer, and an electrode including an organic semiconductor material.

The metal oxide may include copper, nickel, ruthenium, manganese, molybdenum, vanadium, aluminum, tantalum, gold, silver, iridium, iron, cobalt, chromium, tungsten, titanium, palladium, tin, or a combination thereof.

The conductive polymer may include a polyaniline-based, polythiophene-based, polypyrrole-based, polyacetylene-based, polyparaphenylene-based polymer, or a combination thereof.

The film may include a carbon material and an organic semiconductor material.

The carbon material may be activated carbon, an activated carbon fiber, carbon black, graphite, graphene, graphene oxide, carbon aerogel, mesoporous carbon, meso/macroporous carbon, a carbon nanotube, a vapor grown carbon fiber, or a combination thereof.

The carbon material may be a carbon nanotube and the carbon nanotube may be a single-walled or multi-walled carbon nanotube.

The organic semiconductor material may be an organic photoluminescent material.

The organic photoluminescent material may be a monomolecular organic photoluminescent material or a polymeric organic photoluminescent material.

The monomolecular organic photoluminescent material may include anthracene or pyrene.

The polymeric organic photoluminescent material may include an anthracene-based polymer.

The polymeric organic photoluminescent material may be an anthracene-based polymer.

The anthracene-based polymer may include a repeating unit represented by Chemical Formula 1.

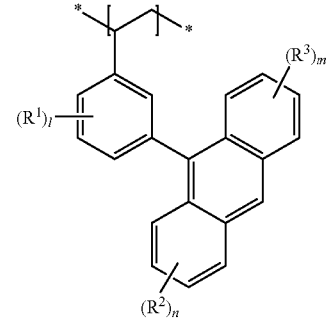

[Chemical Formula 1]

In Chemical Formula 1, $R^1$ to $R^3$ are independently a hydrogen atom, a halogen atom or a substituted or unsubstituted C1 to C10 alkyl group, and l, n, and m are independently an integer ranging from 0 to 4.

The anthracene-based polymer may have a thermal decomposition temperature of 80° C. to 120° C.

The anthracene-based polymer may have a thermal decomposition temperature of 250° C. to 300° C.

The film may further include a surfactant.

An amount of the carbon material and the surfactant may be five times to fifteen times greater than an amount of the organic semiconductor material.

The current collector may be stainless steel.

Another embodiment of the present invention provides a method for manufacturing an electrode including mixing at least one selected from a carbon material, a metal oxide, and a conductive polymer, an organic semiconductor material, and a solvent to prepare a mixture; coating the mixture on a current collector; and drying the coated mixture on the current collector.

The carbon material, the metal oxide, the conductive polymer, the organic semiconductor material, and the current collector are the same as above.

The preparing of the mixture may be mixing of the carbon material, the organic semiconductor material, and the solvent to prepare a mixture.

The mixture may further include a surfactant.

An amount of the carbon material and the surfactant may be five times to fifteen times greater than an amount of the organic semiconductor material.

The coating may be blade coating.

The drying may be performed by heat-treating the coated mixture at 150° C. to 250° C. for 9 hours to 15 hours.

Yet another embodiment of the present invention provides a supercapacitor including the electrode.

The supercapacitor may further include an electrolyte solution and a separator.

The electrolyte solution may include a chloride ion.

Advantageous Effects

The supercapacitor according to the present invention has large specific capacitance and excellent charge and discharge characteristics by using an electrode including a carbon material such as carbon nanotube and an organic semiconductor material such as an anthracene-based polymer.

DETAILED DESCRIPTION OF THE EMBODIMENTS

Figure 1:
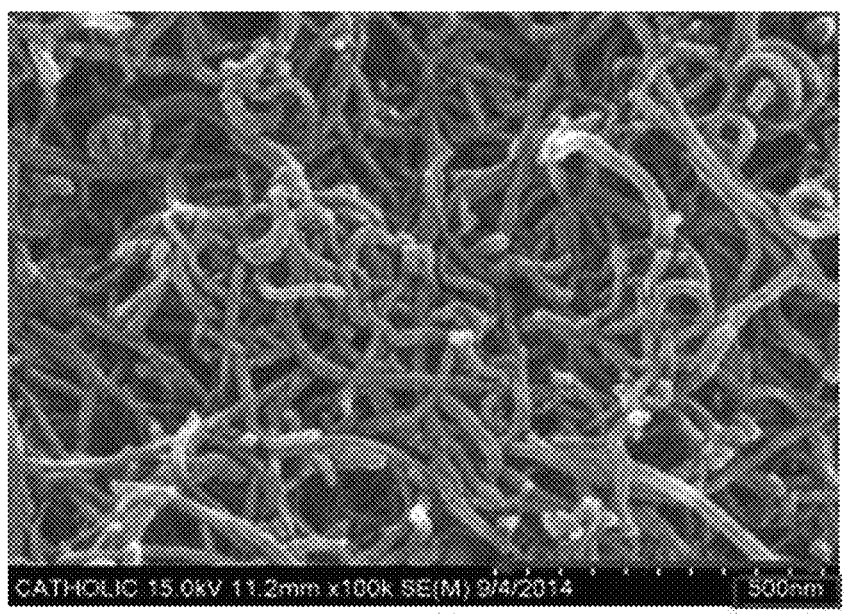
FIG. 1 is a scanning electron microscope (SEM) photograph showing a film inside an electrode according to Comparative Preparation Example 1.

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen by a substituent of a halogen atom (F, Cl, Br, or I), a hydroxy group, a C1 to C20 alkoxy group, a nitro group, a cyano group, an amine group, an imino group, an azido group, an amidino group, a hydrazino group, a hydrazono group, a carbonyl group, a carbamyl group, a thiol group, an ester group, an ether group, a silyl group, a carboxyl group or a salt thereof, a sulfonic acid group or a salt thereof, a phosphoric acid or a salt thereof such as a phosphonic acid, and the like, a C1 to C20 alkyl group, a C2 to C20 alkenyl group, a C2 to C20 alkynyl group, a C6 to C20 aryl group, a C3 to C20 cycloalkyl group, a C3 to C20 cycloalkenyl group, a C3 to C20 cycloalkynyl group, a C2 to C20 heterocycloalkyl group, a C2 to C20 heterocycloalkenyl group, a C2 to C20 heterocycloalkynyl group, a C3 to C20 heteroaryl group, or a combination thereof.

In the present specification, when a definition is not otherwise provided, "hetero" refers to one including at least one heteroatom of N, O, S, and P in Chemical Formula.

In the present specification, when specific definition is not otherwise provided, "a combination" refers to mixing or copolymerization.

In the present specification, when a definition is not otherwise provided, in a chemical formula, hydrogen is bonded at a position when a chemical bond is not drawn where supposed to be given.

In the present specification, when specific definition is not otherwise provided, "*" indicates a point where the same or different atom or Chemical Formula is linked.

An embodiment of the present invention provides an electrode 100 including a current collector 20 and a film 10 located on the current collector, wherein the film includes at least one selected from a carbon material, a metal oxide, and a conductive polymer and an organic semiconductor material.

The electrode 100 according to one embodiment may provide a supercapacitor having large specific capacitance and excellent charge and discharge characteristics by including the film 10 including one selected from a carbon material, a metal oxide, and a conductive polymer, and the organic semiconductor material.

Hereinafter, each component in the electrode is described in details.

The carbon material is an electrode material including carbon, and may be formed into an electric double layer and simultaneously increases electrical conductivity.

Specifically, the carbon material may be activated carbon, an activated carbon fiber, graphite, graphene, graphene oxide, a carbon aerogel, a carbon zerogel, a carbon nanotube, soft carbon (carbon fired at a low temperature), hard carbon, mesoporous carbon, meso/macroporous carbon, fired coke, carbon black, acetylene black, ketjen black, a vapor grown carbon fiber (VGCF), or a combination thereof. For example, the carbon material may be graphene, graphene oxide, carbon nanotube, or a vapor grown carbon fiber and the carbon nanotube may be single-walled carbon nanotube or a multi-walled carbon nanotube.

For example, the carbon nanotube is a material in which hexagons consisting of six carbons are connected with one another and form a pipe shape, and thus have excellent thermal conductivity and strength. The carbon nanotube may be further classified into single-walled carbon nanotube, multi-walled carbon nanotube, and the like, and herein, the single-walled carbon nanotube and multi-walled carbon nanotube have excellent mechanical properties such as (twice to ten times) higher elasticity, (20 times to 700 times) higher tensile strength and the like than steel, and may be usefully used as an electrode material for a supercapacitor, and the like.

The carbon material may be used regardless of size. For example, the carbon nanotube may have an average diameter (a particle diameter of the cross-section) ranging from 10 nm to 100 nm, for example, 10 nm to 50 nm, and for another example, 10 nm to 30 nm.

In the metal oxide, the metal may include copper, nickel, ruthenium, manganese, molybdenum, vanadium, aluminum, tantalum, gold, silver, iridium, iron, cobalt, chromium, tungsten, titanium, palladium, tin, or a combination thereof. For example, the metal may be nickel, ruthenium, manganese, iron, or a combination thereof.

The metal oxide may cause an oxidation-reduction reaction in an electrode. The oxidation-reduction reaction may be caused by the metal oxide with ions of an electrolyte intercalated and deintercalated or adsorbed in the surface of the metal oxide.

The metal oxide may be, for example, nickel oxide, ruthenium oxide, manganese oxide, iron oxide, or a mixed oxide of at least two selected from nickel, ruthenium, manganese, and iron.

The ruthenium oxide may cause a reaction represented by the Reaction Scheme 1 in an acidic electrolyte.

[Reaction Scheme 1]

The manganese oxide may cause a reaction expressed by the following Reaction Scheme 2 in an alkaline electrolyte.

[Reaction Scheme 2]

The ruthenium oxide may realize large specific capacitance. The manganese oxide is inexpensive and environmentally friendly.

The metal oxide may be used regardless of size. For example, the metal oxide may have an average particle diameter ranging from 10 nm to 100 nm, for example, 10 nm to 50 nm, and for another example, 10 nm to 30 nm.

The metal oxide may further include the carbon material.

The metal oxide may be, for example $RuO_2$—$H_2O$, a ruthenic acid nano sheet/Au, $H_{0.2}RuO_{2.1} \cdot nH_2O$ (n is a rational number of greater than 0), $RuO_2$/carbon, amorphous $RuO_{1-y}Cr_yO_2/TiO_2$ (y is a rational number of greater than 0), $MnO_2$, $MnO_2$/activated carbon, $SnO_2$/carbon aerogel, NiOH, NiOH/activated carbon, cobalt-nickel oxide/carbon nanotube, nickel-based mischmetal/activated carbon, $Mo_2N/Ta_2O_5$, $MnFe_2O_4$, TiN, $V_2O_5$, or combination thereof, but is not limited thereto.

The conductive polymer is a polymer having electrical conductivity and generally includes a Π bond. The conductive polymer may be for example a hetero cyclic polymer such as a polyaniline-based, polythiophene-based, polypyrrole-based polymer and the like, or a polyacetylene-based or polyparaphenylene-based polymer, or a combination thereof. In addition, the conductive polymer may further include the carbon material or a metal oxide.

Specifically the conductive polymer may be polyaniline, polyaniline/activated carbon, polyaniline/$MnO_2$, poly-3,4-ethylenedioxythiophene (PEDOT), poly(3-methylthiophene), poly(3-methylthiophene)/$MnO_2$, polypyrrole, polypyrrole/activated carbon, poly(fluorophenylthiophene), poly(isothianaphthene), or a combination thereof, but is not limited thereto.

The polyaniline-based polymer and polypyrrole-based polymer may realize large specific capacitances. The polyaniline-based polymer may realize a larger specific capacitance than the polypyrrole-based polymer by 50 F/g to 110 F/g.

The organic semiconductor material may be an organic photoluminescent material.

The organic photoluminescent material may be a monomolecular organic photoluminescent material or a polymeric organic photoluminescent material.

The monomolecular organic photoluminescent material may include anthracene or pyrene and the polymeric organic photoluminescent material may include an anthracene-based polymer.

The polymeric organic photoluminescent material may be an anthracene-based polymer.

The anthracene-based polymer may include a repeating unit represented by Chemical Formula 1.

[Chemical Formula 1]

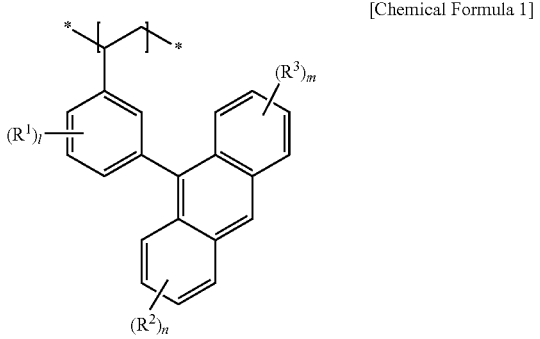

In Chemical Formula 1, $R^1$ to $R^3$ are independently a hydrogen atom, a halogen atom or a substituted or unsubstituted C1 to C10 alkyl group, and l, n, and m are independently an integer ranging from 0 to 4.

The anthracene-based polymer is a main light emitting material used in an organic light emitting diode device and has excellent oxidation stability, and thus may secure high stability and long life-span characteristics during operation of a device. Accordingly, when the anthracene-based polymer including a repeating unit represented by the above Chemical Formula 1 is used as an electrode material, a supercapacitor including the electrode material may have large specific capacitance and excellent charge and discharge efficiency.

The anthracene-based polymer may have a glass transition temperature of 80° C. to 120° C. and a thermal decomposition temperature of 250° C. to 300° C. When the anthracene-based polymer has a glass transition temperature and a thermal degradation temperature within the ranges, the anthracene-based polymer has high thermal stability and thus may secure excellent life-span characteristics of a supercapacitor.

The anthracene-based polymer may have a weight average molecular weight of 1,000 g/mol to 100,000 g/mol.

The carbon material and the organic semiconductor material such as anthracene-based polymer and the like may be included in a weight ratio of 1:5 to 5:1, for example 1:3 to 3:1.

In addition, the carbon material and a surfactant (the total content of the carbon material and the surfactant) may be used at 5 times to 15 times, for example, 7 times to 12 times, and for another example, 8 times to 10 times greater amount than that of the organic semiconductor material such as an anthracene-based polymer. (That is, "the carbon material and the surfactant":"the organic semiconductor material such as an anthracene-based polymer" are used in a weight ratio ranging from 5:1 to 15:1, for example, 7:1 to 12:1, and for another example, 8:1 to 10:1). When the carbon material and the surfactant are included within the weight ratio, an electrode and a supercapacitor including this electrode may realize excellent capacitance, life-span characteristic, and stability, and also excellent charge and discharge efficiency, since ions are smoothly exchanged as the carbon material has a larger pore size and thus an increased specific surface.

The film 10 included in the electrode 100 according to one embodiment may further include a surfactant, for example, a Triton-based surfactant, for example Triton X-100, and the like, other than the carbon material and the organic semiconductor material such as an anthracene-based polymer.

When the surfactant is further included, the carbon material and the organic semiconductor material such as an anthracene-based polymer and the like may be uniformly dispersed.

The current collector 20 included in the electrode 100 according to one embodiment may be a material having conductivity without a particular limit, for example, stainless steel, platinum, gold, copper, carbon series, ITO (In doped $SnO_2$), FTO (F doped $SnO_2$), and the like. For example, the current collector may be stainless steel.

The electrode 100 according to one embodiment may include one selected from a carbon material, a metal oxide, and a conductive polymer, and an anthracene-based polymer and/or a surfactant, which are uniformly dispersed on the current collector 20.

The electrode 100 according to one embodiment has excellent electrical conductivity and excellent particle uniformity and thus may be appropriately used for a supercapacitor.

Another embodiment of the present invention provides a method of manufacturing an electrode including: mixing one selected from a carbon material, a metal oxide, and a conductive polymer, and an organic semiconductor material and a solvent to prepare a mixture; coating the mixture on a current collector 20; and drying the mixture coated on the current collector.

The carbon material, metal oxide, conductive polymer, organic semiconductor material, and current collector are the same as aforementioned, and the solvent may be a solvent generally used in a field related to the present invention. For example, the solvent may be an aqueous- or organic-based solvent. That is, the solvent may be water, an alcohol-based, amide-based, carbonate-based, or aromatic hydrocarbon-based solvent, or a combination thereof. Specific examples of the solvent may be water, methanol, ethanol, dimethyl formamide (DMF), or a combination thereof.

Hereinafter, a method of manufacturing the electrode is illustrated step-by-step in detail.

The method for manufacturing an electrode may include mixing at least one selected from a carbon material, a metal oxide, and a conductive polymer, an organic semiconductor material, and a solvent to prepare a mixture.

The manufacturing method may provide an electrode in which one selected from a carbon material, a metal oxide, and a conductive polymer, and the organic semiconductor material, are uniformly dispersed.

For example, the mixture may be prepared by mixing a carbon material, an organic semiconductor material, and a solvent and further include a surfactant, for example, a Triton-based surfactant, for example Triton X-100 and the like.

The carbon material and the organic semiconductor material such as an anthracene-based polymer may be mixed in an appropriate ratio depending on a use and a purpose. For example, the carbon material and the organic semiconductor material such as an anthracene-based polymer may be included in a weight ratio of 1:5 to 5:1, for example 1:3 to 3:1.

In addition, the carbon material and the surfactant (the total amount of the carbon material and the surfactant) may be included at 5 times to 15 times, for example, 7 times to 12 times, and for another example, 8 times to 10 times, greater amount than that of the organic semiconductor material such as an anthracene-based polymer. (That is, "carbon material and surf actant":"organic semiconductor material such as an anthracene-based polymer" are mixed in a weight ratio of 5:1 to 15:1, for example, 7:1 to 12:1, and for another example, 8:1 to 10:1). When mixed within the weight ratio and the amount ratio, an electrode and a supercapacitor including the same may realize excellent capacitance, life-span characteristics, and stability.

A method for manufacturing the electrode includes mixing the electrode material (at least one selected from a carbon material, a metal oxide, and a conductive polymer, an organic semiconductor material, and/or a surfactant) with a solvent to prepare a mixture and then coating the mixture on a current collector 20.

The coating may include spin coating, roll coating, Meyer bar coating, blade coating, gravure coating, reverse gravure coating, kiss reverse coating, die coating, comma coating, or the like. For example, the coating may be blade coating.

In addition, the method may include drying and removing the solvent after coating the mixture on the current collector 20. In this way, when the solvent is removed, a film in which the electrode material is uniformly mixed and distributed on the current collector 20 may be formed.

The step of drying may be performed by heat-treating at 150° C. to 250° C. for 9 hours to 15 hours, for example at 180° C. to 220° C. for 10 hours to 14 hours.

Another embodiment of the present invention provides a supercapacitor including the electrode.

The supercapacitor may further include an electrolyte solution and a separator. The supercapacitor has very large specific capacitance and excellent charge and discharge characteristics.

The supercapacitor includes the above electrode and all the other same constituents as a general supercapacitor.

The electrolyte solution used in the present invention may include any electrolyte solution capable of causing an electrochemical reaction with an electrode without a particular limit. For specific examples, the electrolyte solution may include $H_2SO_4$, $Na_2SO_4$, $(NH_4)_2SO_4$, KOH, LiOH, $LiClO_4$, KCl, $Li_2SO_4$, KOH, NaOH, NaCl, and the like, and may further include manganese oxide ($MnO_2$, $Mn_2O_3$, or $Mn_3O_4$), nickel oxide (NiO), vanadium oxide ($V_2O_5$), tungsten oxide ($WO_3$), cobalt oxide (CoO, $Co_2O_3$, or $Co_3O_4$), molybdenum oxide ($MoO_3$), or a combination thereof.

Specifically, the electrolyte solution may include chloride ions. When the electrolyte solution in the supercapacitor includes chloride ions, large specific capacitance and excellent charge and discharge efficiency are obtained.

The separator may be a polyethylene or polypropylene-containing film laminate, or a cellulose, polyester, or polypropylene-containing fiber non-woven fabric as a porous insulating material.

Hereinafter, examples of the present invention and comparative examples are described. These examples, however, are not in any sense to be interpreted as limiting the scope of the invention.

EXAMPLES

Synthesis of Organic Semiconductor Material

Synthesis Example 1

Synthesis of Anthracene-based Polymer

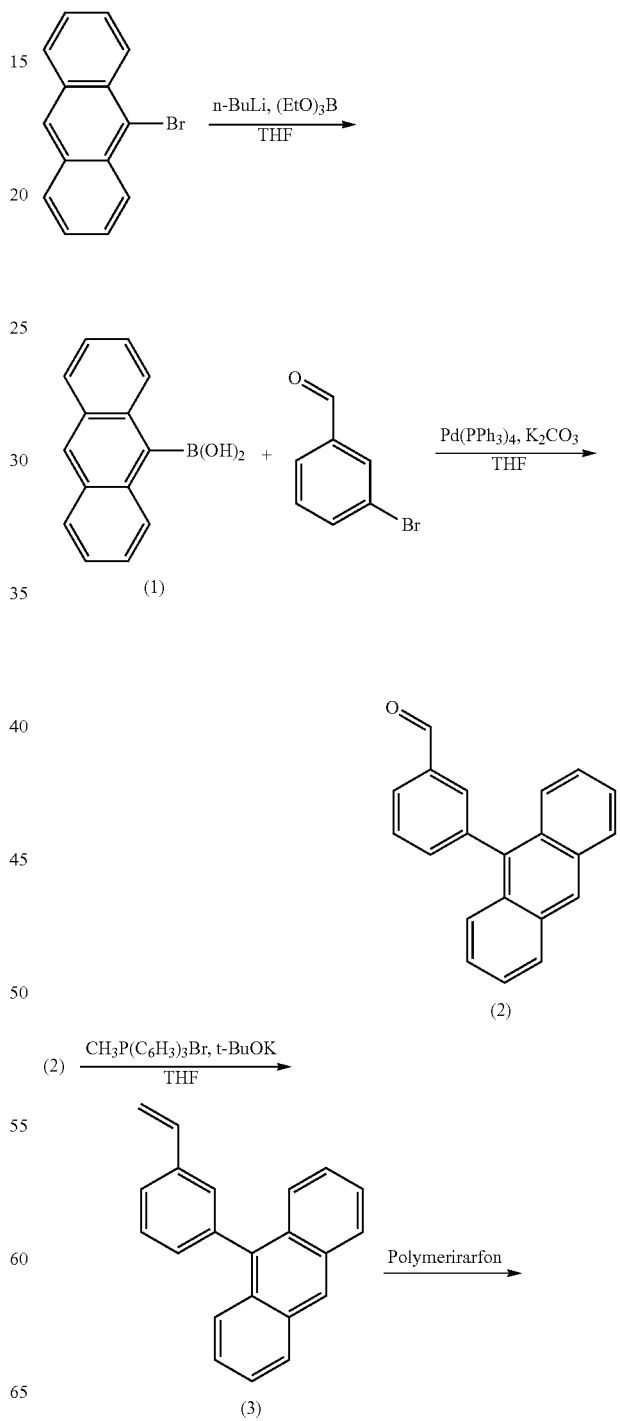

-continued

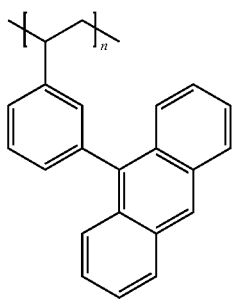

Synthesis of Intermediate (1)

(Synthesis of Anthracen-10-yl-10-boronic acid)

9-bromoanthracene (10 g, 38.9 mmol) was dissolved in 500 mL of anhydrous THF, and the solution was cooled down to −78° C. Then, 1.6 M n-BuLi (29.3 mL, 46.7 mmol) and triethyl borate (9.3 mL, 54.5 mmol) were added thereto, and the mixture was agitated for 30 minutes. When the reaction was complete, 2N HCl was added thereto, and the mixture was treated with ethyl acetate and water for extraction. Then, anhydrous MgSO$_4$ was added thereto to remove moisture, a product obtained therefrom was filtered, and a solvent was removed. Hexane and ethyl acetate (50 mL) were used to perform reprecipitation. A precipitate therein was filtered, obtaining a colorless material (Intermediate (1)).

$^1$H-NMR (300 MHz, CDCl$_3$) δ (ppm): 8.46 (s, 1H), 8.12 (d, 2H), 8.01 (d, 2H), 7.48 (m, 4H), 5.07 (s, 2H)

Synthesis of Intermediate (2)

(Synthesis 3-(Anthracen-10-yl)benzaldehyde)

Intermediate (1) (7.2 g, 32 mmol), 3-bromoaldehyde (3.15 mL, 27 mmol), and Pd(PPh$_3$)$_4$ (1.25 g, 1.1 mmol) were put in a 500 mL round-bottomed flask under an N$_2$ condition, and anhydrous THF was added thereto. The temperature of the flask was increased up to 80° C., and K$_2$CO$_3$ was put in the flask. When the reaction was complete, the resulting mixture was treated with toluene and water for extraction. Then, anhydrous MgSO$_4$ was used to remove moisture therefrom. The mixture after the synthesis was column-purified under a condition of toluene:hexane (volume ratio=1:2). The resultant was recrystallized, obtaining a yellow material (Intermediate (2)).

$^1$H-NMR (300 MHz, THF) δ (ppm): 10.09 (s, 1H), 8.60 (s, 1H), 8.11-8.07 (d, 3H), 7.96-7.95 (s, 1H), 7.83-7.78 (t, 1H), 7.73-7.69 (m, 1H), 7.57-7.54 (d, 2H), 7.48-7.43 (t, 2H), 7.37-7.34 (m, 2H)

Synthesis of Intermediate (3)

(Synthesis of 10-(3-vinylphenyl) anthracene)

Methyltriphenyl phosphonium bromide and KOC(CH$_3$)$_3$ (3.18 g, 28 mmol) were added to 200 mL of anhydrous THF, and the mixture was maintained at 0° C. Then, Intermediate (2) (5 g, 17.7 mmol) was added thereto. When the reaction was complete, methylene chloride and water were used for extraction. Then, anhydrous MgSO$_4$ was used to remove moisture therefrom. The mixture after the synthesis was column-purified under a condition of chloroform:hexane (volume ratio=1:10). The resultant was reprecipitated, obtaining a yellow material (Intermediate (3)).

$^1$H-NMR (300 MHz, THF) δ (ppm): 8.54 (s, 1H), 8.07-8.04 (d, 2H), 7.64-7.60 (m, 3H), 7.58-7.53 (t, 1H), 7.50 (s, 1H), 7.46-7.40 (t, 2H), 7.35-7.32 (m, 3H), 6.87-6.78 (d, 1H), 5.87-5.81 (dd, 1H), 5.27-5.23 (dd, 1H)

Synthesis of Anthracene-based Polymer (Synthesis of Poly (9-(3-Vinyl-phenyl)-anthracene) (PVPA))

Intermediate (3) (0.2 g, 0.7 mmol) and azobisisobutyronitrile (0.07 g, 0.42 mmol) were put in a 100 mL round-bottomed flask, and anhydrous benzene was added thereto. The mixture was agitated at 50° C. for 6 hours to perform a polymer reaction, and a polymer produced therein was precipitated by using methanol. Then, chloroform and methanol were used to perform reprecipitation, obtaining an anthracene-based polymer (PVPA; poly(9-(3-vinyl-phenyl)-anthracene)).

$^1$H-NMR (300 MHz, THF) δ (ppm): 7.61-6.81 (broad peaks, aromatic rings), 1.48-1.04 (alkyl groups)

The anthracene-based polymer (PVPA) according to Synthesis Example 1 had a weight average molecular weight ranging from 4000 g/mol to 5000 g/mol, a glass transition temperature of 105° C., and a thermal degradation temperature of 285° C.

Manufacture of Electrode

Preparation Example 1

2.5 g of the anthracene-based polymer Synthesis Example 1, 3 g of multi-walled carbon nanotube, and 20 g of Triton X-100 were dispersed into water, preparing a mixed solution. The mixed solution was blade-coated on a piece of stainless steel. Then, the coated stainless steel was heat-treated (baked) at 200° C. for 12 hours in a vacuum oven to remove moisture to form a film thereon, manufacturing an electrode.

Comparative Preparation Example 1

An electrode was manufactured according to the same method as Preparation Example 1, except for using no anthracene-based polymer according to Synthesis Example 1.

Manufacture of Half Cell

Example 1

The electrode according to Preparation Example 1 as a working electrode, 0.1 M KCl as a electrolyte solution, platinum (Pt) as a counter electrode, and Ag/AgCl as a reference electrode were used to manufacture a half cell.

Example 2

A half cell was manufactured according to the same method as Example 1, except for using KOH instead of the KCl as the electrolyte solution.

Example 3

A half cell was manufactured according to the same method as Example 1, except for using NaCl instead of the KCl as the electrolyte solution.

Example 4

A half cell was manufactured according to the same method as Example 1, except for using $Na_2SO_4$ instead of the KCl as the electrolyte solution.

Example 5

A half cell was manufactured according to the same method as Example 1, except for using NaOH instead of the KCl as the electrolyte solution.

Comparative Example 1

A half cell was manufactured according to the same method as Example 1, except for using the electrode according to Comparative Preparation Example 1 instead of the electrode according to Preparation Example 1.

Comparative Example 2

A half cell was manufactured according to the same method as Example 2, except for using the electrode according to Comparative Preparation Example 1 instead of the electrode according to Preparation Example 1.

Comparative Example 3

A half cell was manufactured according to the same method as Example 3, except for using the electrode according to Comparative Preparation Example 1 instead of the electrode according to Preparation Example 1.

Comparative Example 4

A half cell was manufactured according to the same method as Example 4, except for using the electrode according to Comparative Preparation Example 1 instead of the electrode according to Preparation Example 1.

Comparative Example 5

A half cell was manufactured according to the same method as Example 5, except for using the electrode according to Comparative Preparation Example 1 instead of the electrode according to Preparation Example 1.

(Evaluation)

Experimental Example 1

Scanning Electron Microscope

Figure 2:
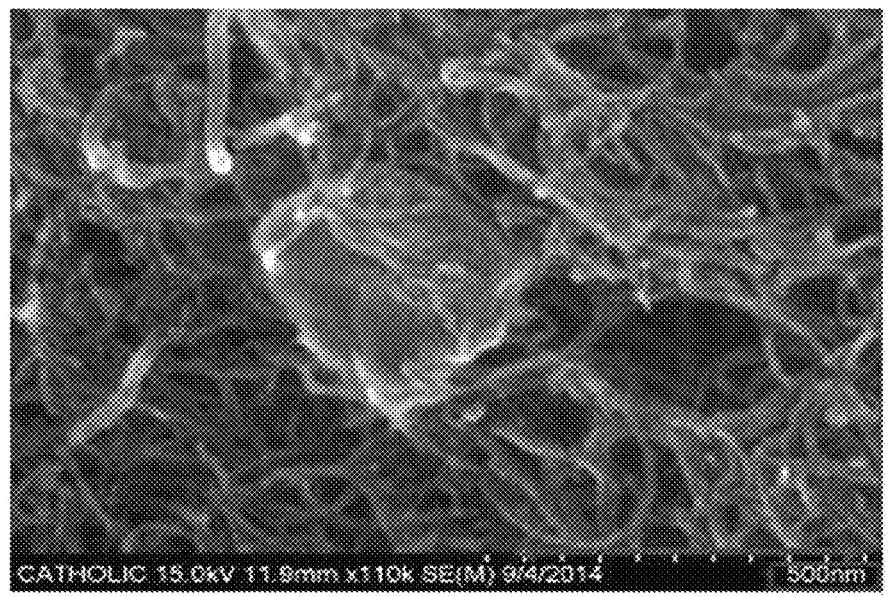
FIG. 2 is a scanning electron microscope (SEM) photograph showing a film inside an electrode according to Preparation Example 1.

Scanning electron microscope (SEM) photographs of the electrodes according to Preparation Example 1 and Comparative Preparation Example 1 are provided in FIGS. 1 to 5. FIG. 1 is a scanning electron microscope photograph showing a film in the electrode according to Comparative Preparation Example 1, and FIG. 2 is a scanning electron microscope photograph showing a film in the electrode according to Preparation Example 1. FIG. 1 shows that no anthracene-based polymer was present in the electrode according to Comparative Preparation Example 1, and FIG. 2 shows that the multi-walled carbon nanotube and the anthracene-based polymer were evenly dispersed on a current collector in the electrode according to Preparation Example 1.

Compared with FIG. 1, the electrode according to Preparation Example 1 was washed with a methylene chloride washing solution to see whether a particle seen only in FIG. 2 was an anthracene-based polymer or not.

Figure 3:
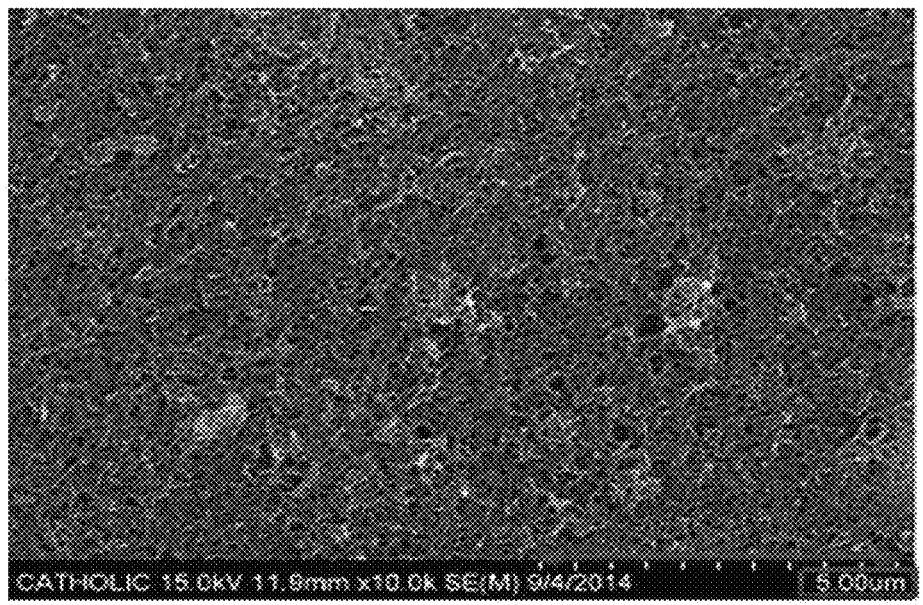
FIGS. 3 to 5 are scanning electron microscope (SEM) photographs showing the film inside the electrode according to Preparation Example 1 after washing it with methylene chloride.
Figure 4:
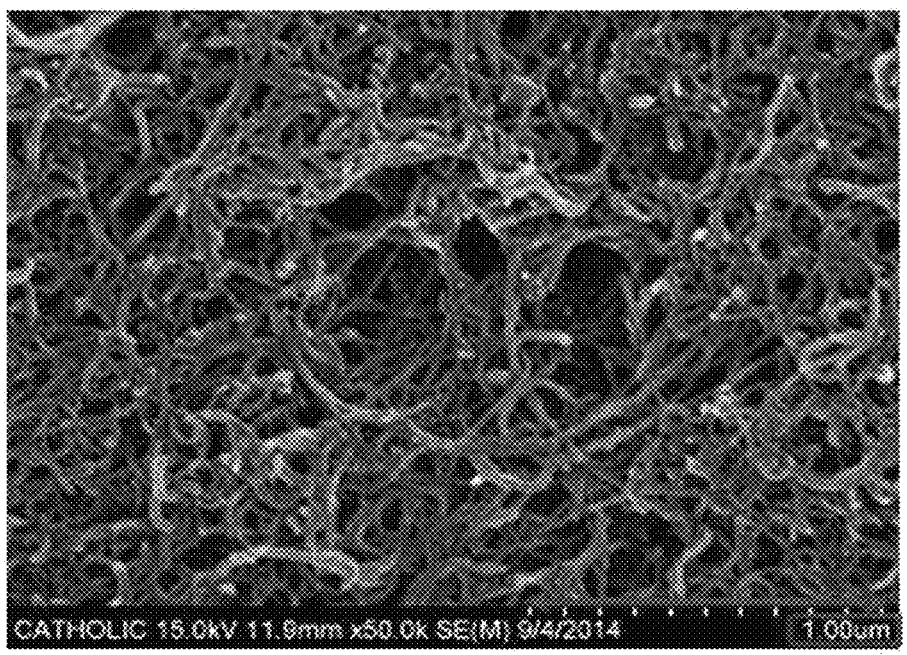
Figure 5:
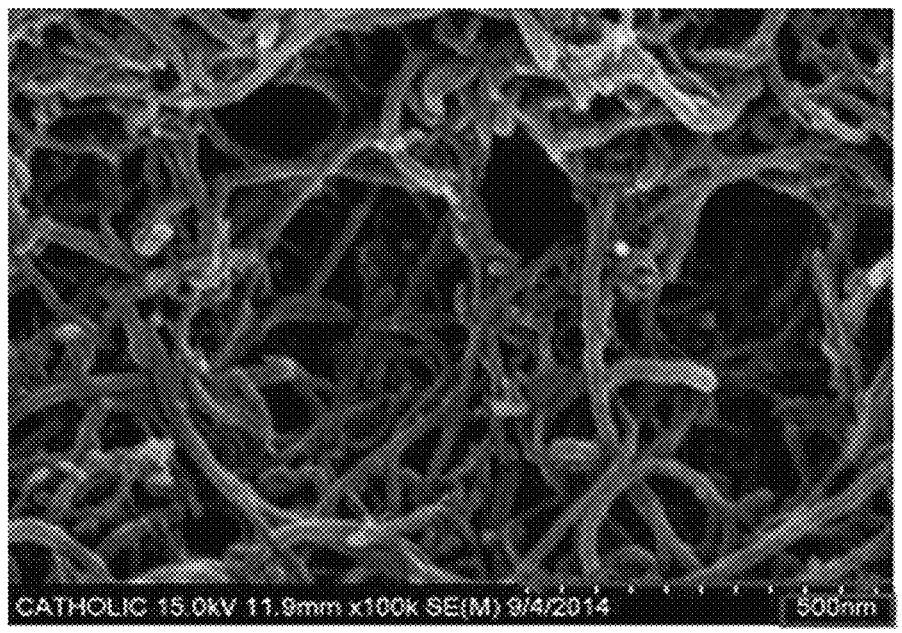

FIGS. 3 to 5 show the scanning electron microscope photographs of the particle after the washing. Referring to FIGS. 3 to 5, an empty space was present in the multi-walled carbon nanotube, and accordingly, the anthracene-based polymer turned out to be dissolved in the methylene chloride washing solution.

Figure 6:
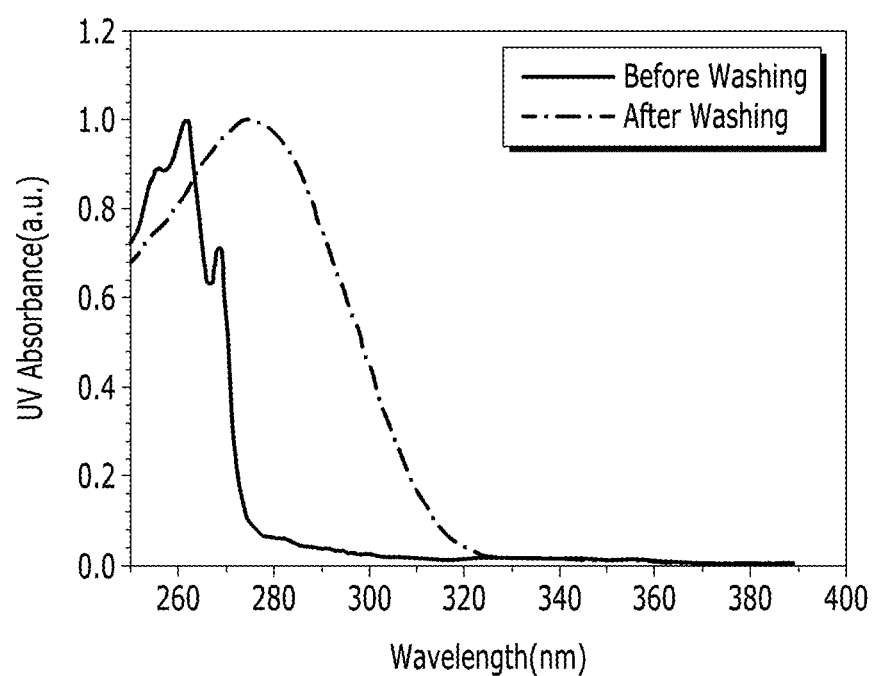
FIG. 6 is a graph showing UV absorbance before and after washing the film inside the electrode according to Preparation Example 1 with methylene chloride.
Figure 7:
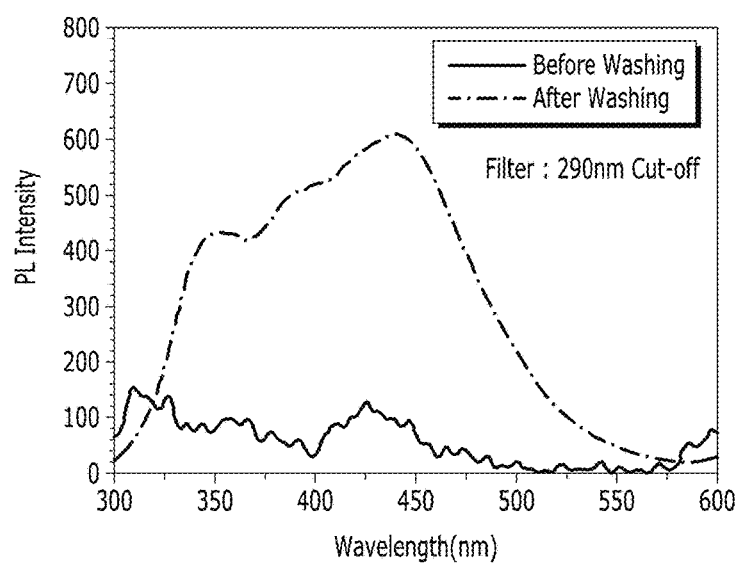
FIG. 7 is a graph showing PL intensity before and after washing the film inside the electrode according to Preparation Example 1 with methylene chloride.
Figure 8:
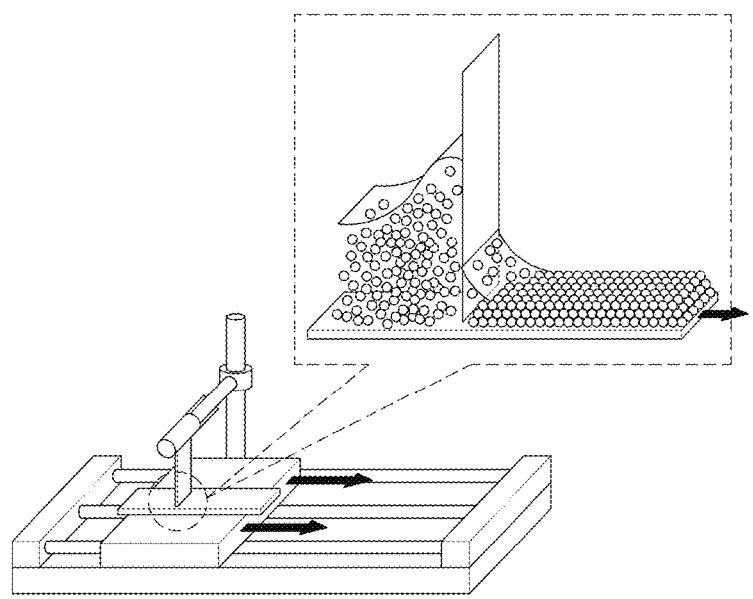
FIG. 8 is a schematic view showing a method of blade-coating a film according to one embodiment on a current collector.
Figure 9:
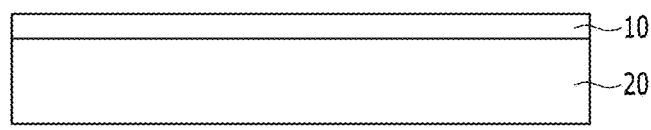
FIG. 9 is a schematic view showing an electrode according to one embodiment.

In addition, FIGS. 6 and 7 are graphs showing UV absorbance and PL intensity of the electrode according to Preparation Example 1 before and after the washing with the methylene chloride washing solution. Referring to FIGS. 6 and 7, the anthracene-based polymer caused additional UV absorption and light emission after the washing. In other words, FIGS. 6 and 7 show that the anthracene-based polymer was well mixed in the film inside the electrode according to Preparation Example 1.

Experimental Example 2

Evaluation of Electrochemical Characteristics

Figure 10A:
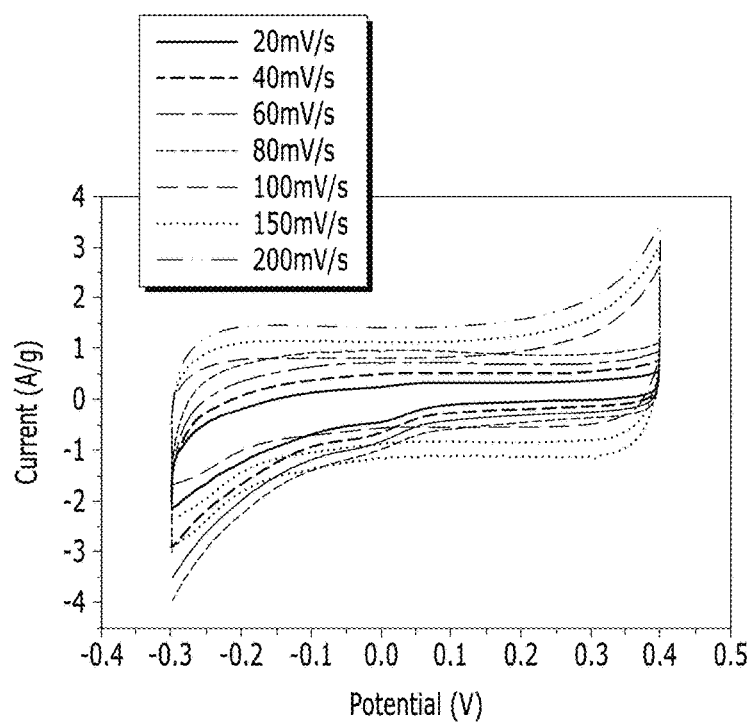
FIGS. 10A and 10B are respectively a voltage-current graph and a charge-discharge graph of an electrode according to Example 1 under a KCl electrolyte solution condition.
Figure 11A:
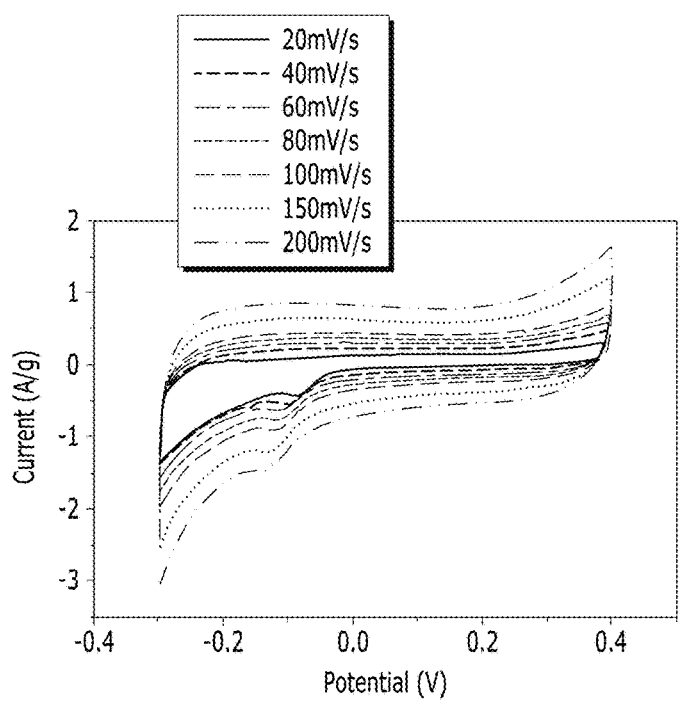
FIGS. 11A and 11B are respectively a voltage-current graph and a charge-discharge graph of an electrode according to Comparative Example 1 under a KCl electrolyte solution condition.
Figure 12A:
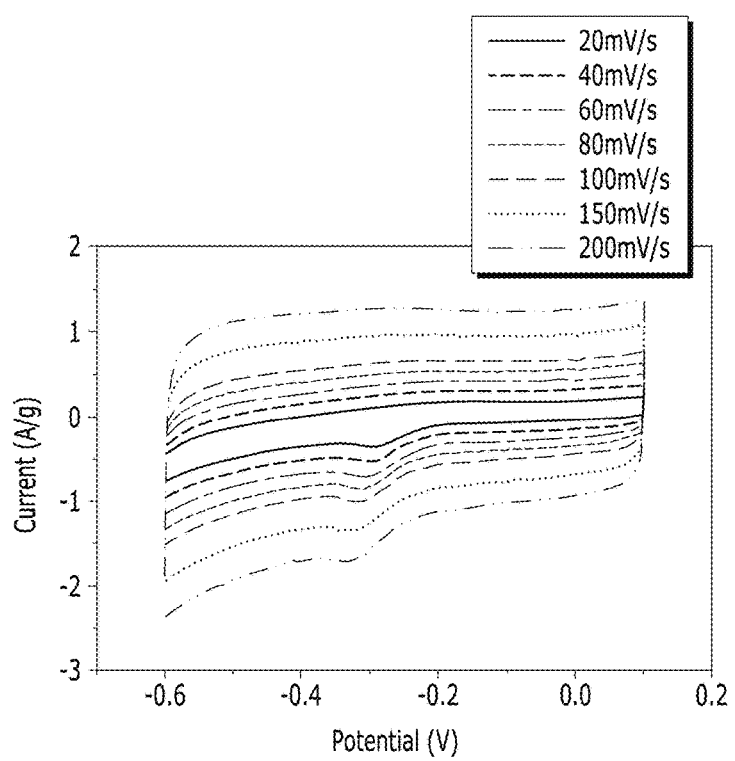
FIGS. 12A and 12B are respectively a voltage-current graph and a charge-discharge graph of an electrode according to Example 2 under a KOH electrolyte solution condition.
Figure 13A:
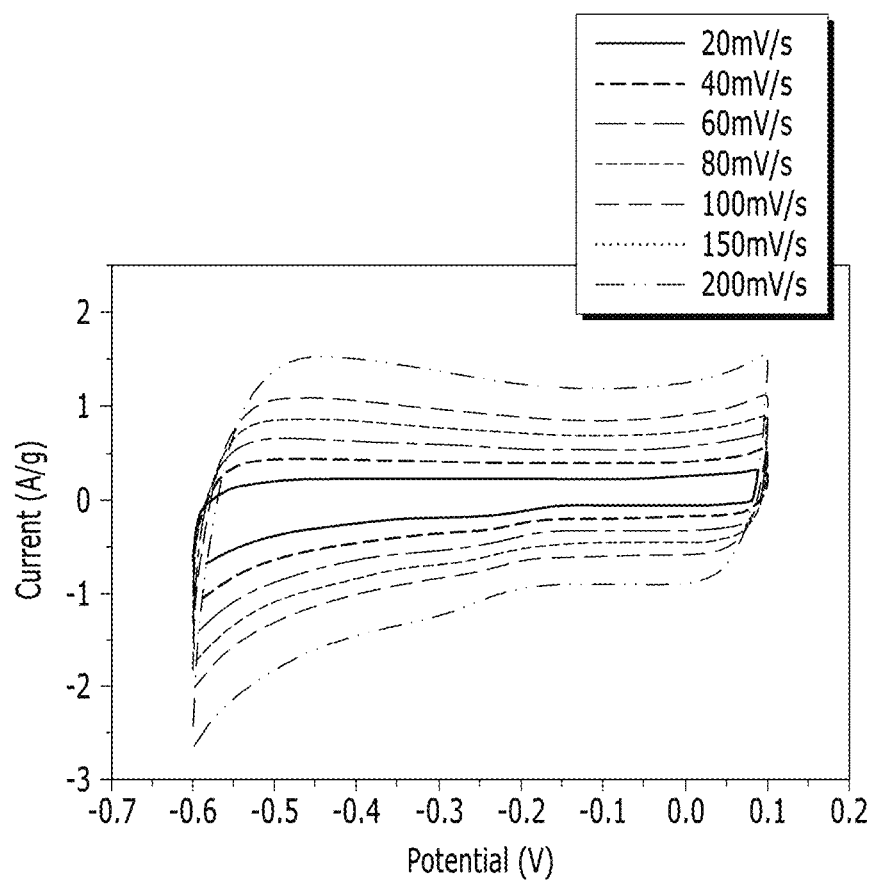
FIGS. 13A and 13B are respectively a voltage-current graph and a charge-discharge graph of an electrode according to Comparative Example 2 under a KOH electrolyte solution condition.
Figure 14A:
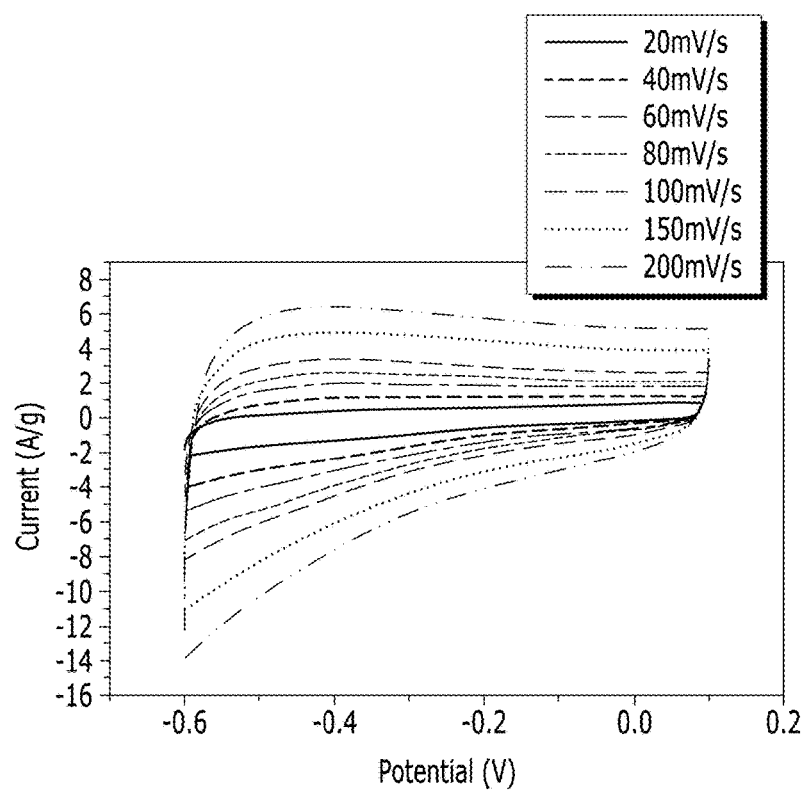
FIGS. 14A and 14B are respectively a voltage-current graph and a charge-discharge graph of an electrode according to Example 3 under a NaCl electrolyte solution condition.
Figure 15A:
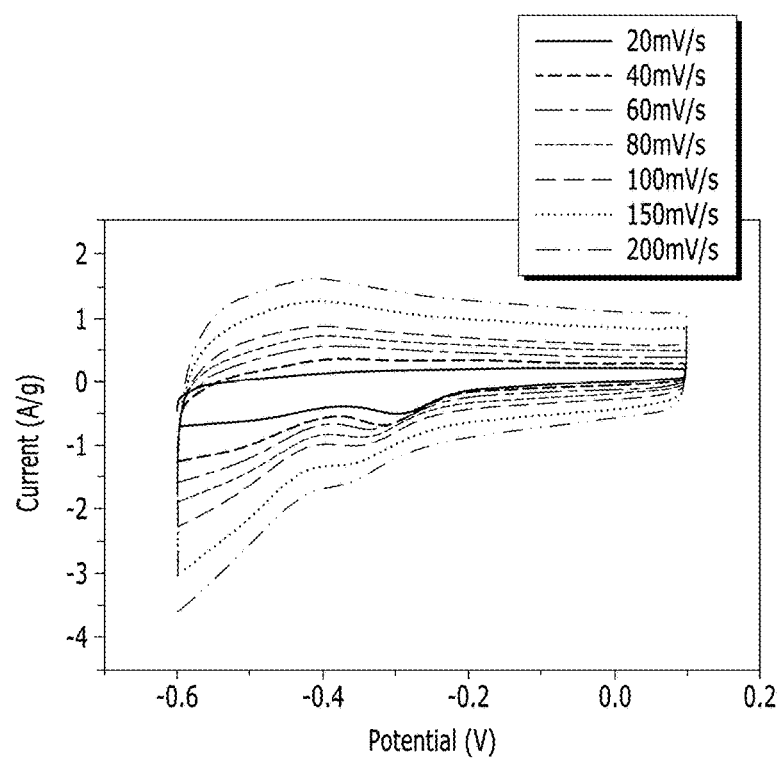
FIGS. 15A and 15B are respectively a voltage-current graph and a charge-discharge graph of an electrode according to Comparative Example 3 under a NaCl electrolyte solution condition.
Figure 16A:
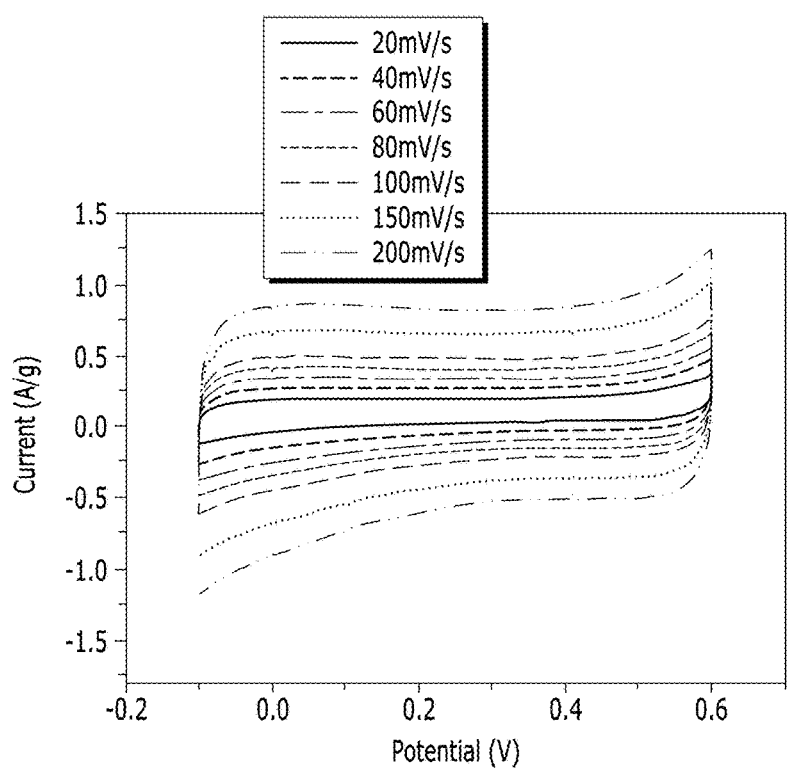
FIGS. 16A and 16B are respectively a voltage-current graph and a charge-discharge graph of an electrode according to Example 4 under a $Na_2SO_4$ electrolyte solution condition.
Figure 17A:
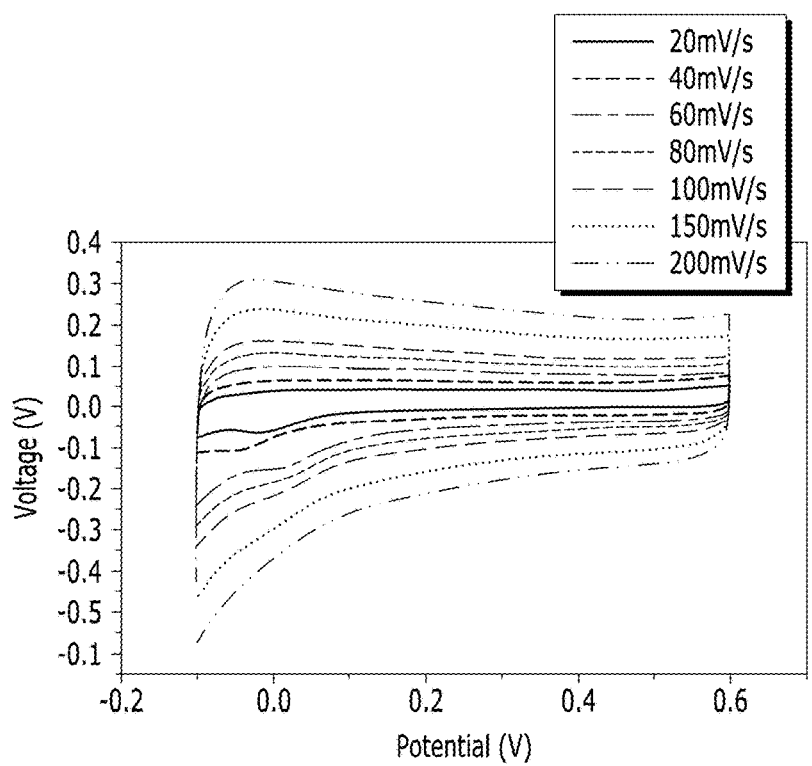
FIGS. 17A and 17B are respectively a voltage-current graph and a charge-discharge graph of an electrode according to Comparative Example 4 under a $Na_2SO_4$ electrolyte solution condition.
Figure 18A:
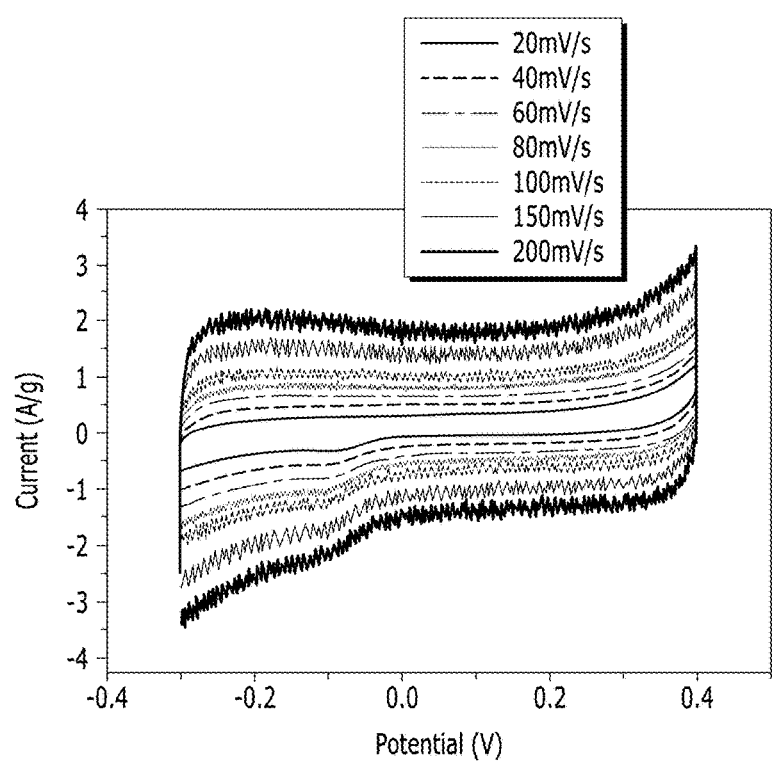
FIGS. 18A and 18B are respectively a voltage-current graph and a charge-discharge graph of an electrode according to Example 5 under a NaOH electrolyte solution condition.
Figure 19A:
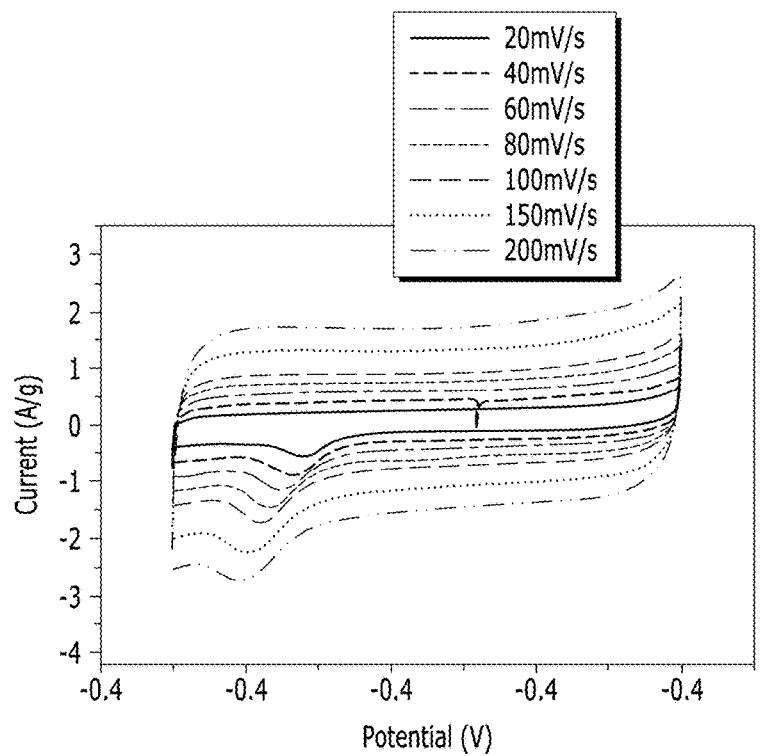
FIGS. 19A and 19B are respectively a voltage-current graph and a charge-discharge graph of an electrode according to Comparative Example 5 under a NaOH electrolyte solution condition.

Electrochemical characteristics of a supercapacitor according to Example 1 were evaluated by measuring its circulating current. FIG. 10A (Example 1), FIG. 11A (Comparative Example 1), FIG. 12A (Example 2), FIG. 13A (Comparative Example 2), FIG. 14A (Example 3), FIG. 15A (Comparative Example 3), FIG. 16A (Example 4), FIG. 17A (Comparative Example 4), FIG. 18A (Example 5), and FIG. 19A (Comparative Example 5) respectively show curves of the circulating currents measured at each scan rate of 20 mV/s, 40 mV/s, 60 mV/s, 80 mV/s, 100 mV/s, 150 mV/s, and 200 mV/s, and Tables 1 and 2 show specific capacitance depending on each scan rate. Specifically, Table 1 shows specific capacitances of Examples 1 to 5, and Table 2 shows specific capacitances of Comparative Examples 1 to 5.

Figure 20:
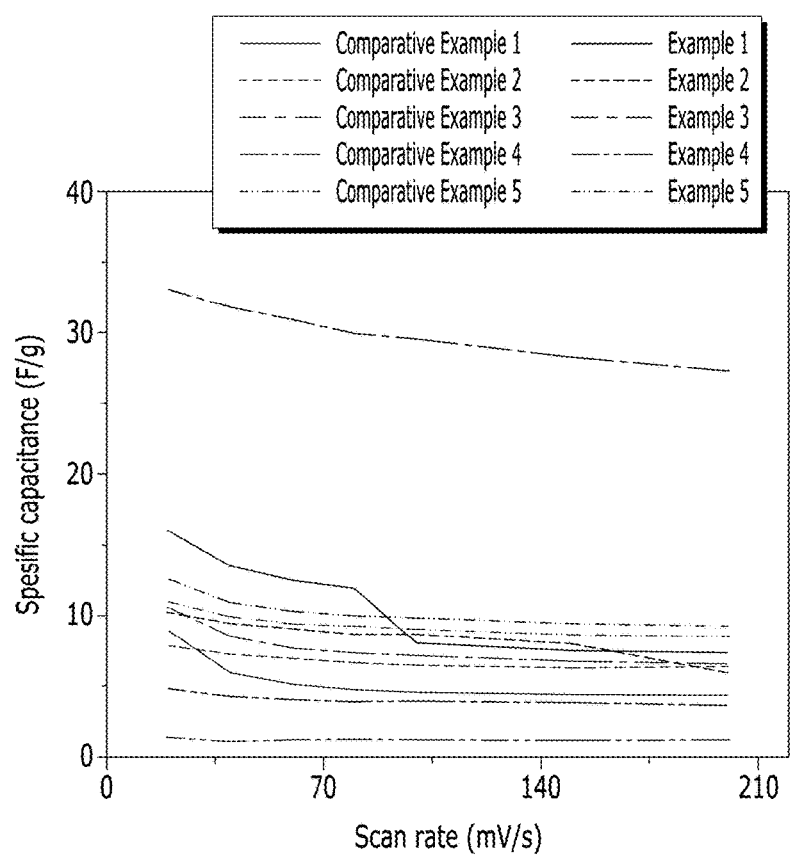
FIG. 20 is a graph showing specific capacitance of the electrodes according to Examples 1 to 5 and Comparative Examples 1 to 5.

On the other hand, FIG. 20 is a graph showing specific capacitance of Examples 1 to 5 and Comparative Examples 1 to 5 depending on a scan rate.

TABLE 1

| | Specific capacitance (F/g) | | | | |
|---|---|---|---|---|---|
| Scan rate | Example 1 | Example 2 | Example 3 | Example 4 | Example 5 |
| 20 | 15.94 | 10.24 | 33.07 | 4.80 | 12.50 |
| 40 | 13.51 | 9.48 | 31.76 | 4.33 | 10.94 |
| 60 | 12.51 | 9.13 | 30.97 | 4.12 | 10.33 |
| 80 | 11.99 | 8.85 | 29.99 | 3.99 | 9.98 |
| 100 | 8.11 | 8.66 | 29.59 | 3.94 | 9.76 |
| 150 | 7.60 | 8.02 | 28.25 | 3.83 | 9.46 |
| 200 | 7.32 | 6.01 | 27.29 | 3.74 | 9.25 |

TABLE 2

| | Specific capacitance (F/g) | | | | |
|---|---|---|---|---|---|
| Scan rate | Comparative Example 1 | Comparative Example 2 | Comparative Example 3 | Comparative Example 4 | Comparative Example 5 |
| 20 | 8.70 | 7.85 | 10.80 | 1.39 | 11.07 |
| 40 | 6.11 | 6.21 | 6.61 | 1.23 | 9.95 |
| 60 | 5.17 | 6.99 | 7.80 | 1.31 | 9.51 |
| 80 | 4.78 | 6.80 | 7.35 | 1.28 | 9.26 |
| 100 | 4.57 | 6.71 | 7.16 | 1.26 | 9.05 |

TABLE 2-continued

| | Specific capacitance (F/g) | | | | |
|---|---|---|---|---|---|
| Scan rate | Comparative Example 1 | Comparative Example 2 | Comparative Example 3 | Comparative Example 4 | Comparative Example 5 |
| 150 | 4.39 | 6.54 | 6.69 | 1.22 | 8.67 |
| 200 | 4.29 | 6.43 | 6.44 | 1.19 | 8.40 |

Figure 10B:
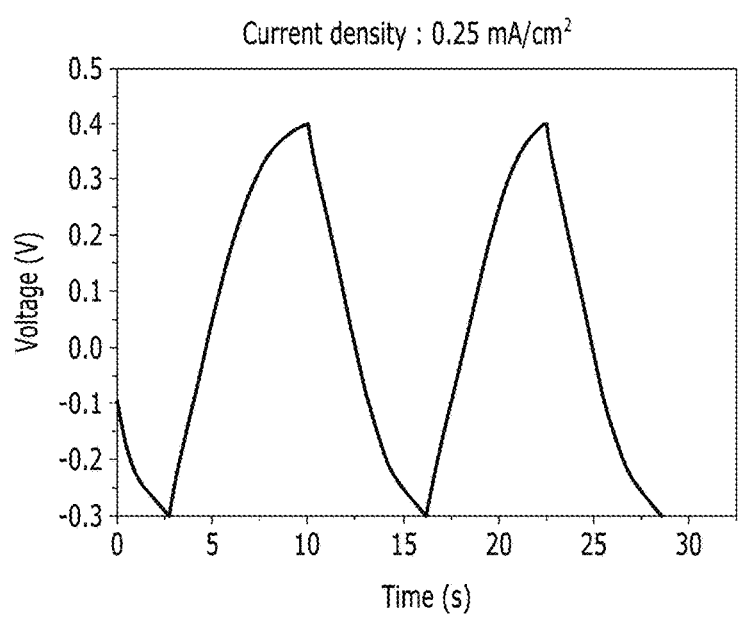
Figure 11B:
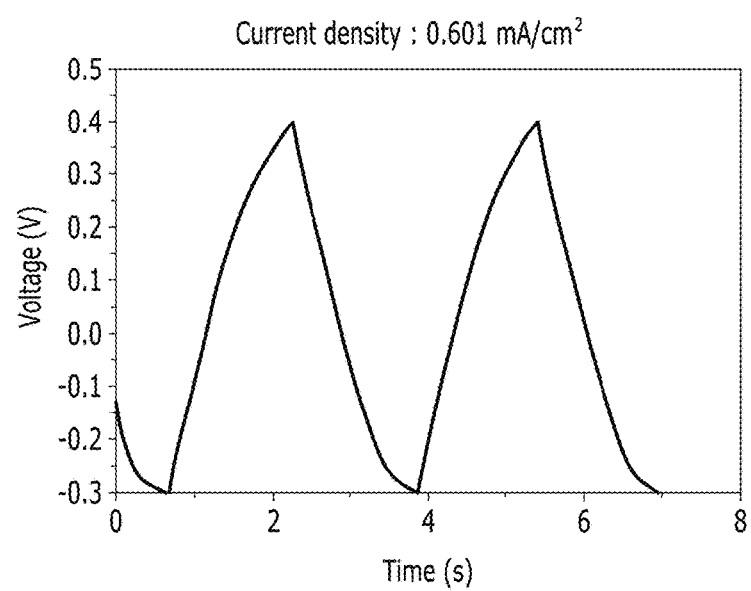
Figure 12B:
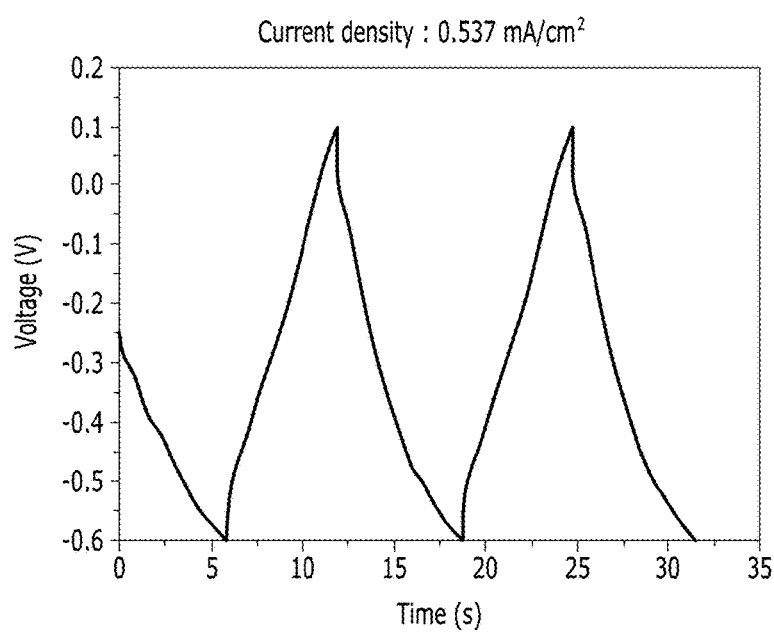
Figure 13B:
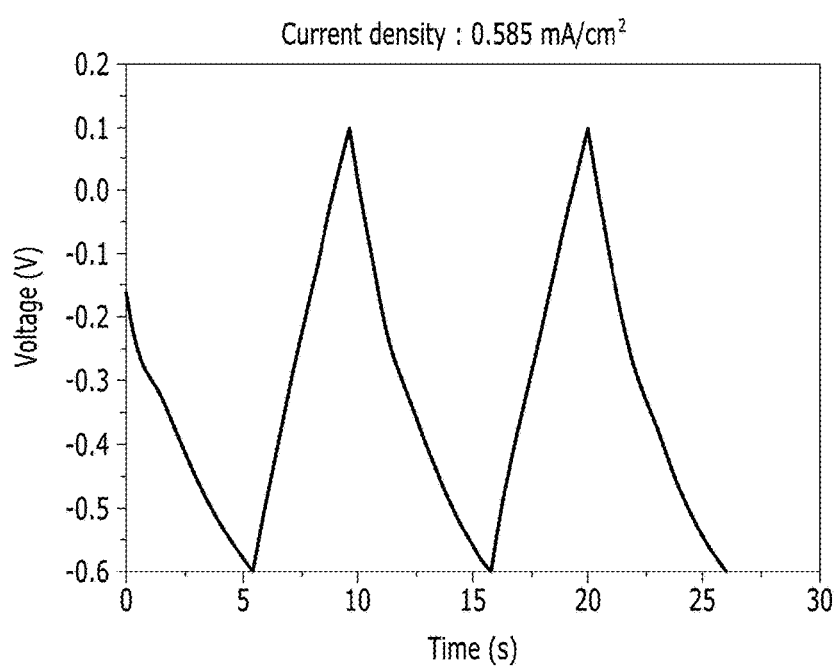
Figure 14B:
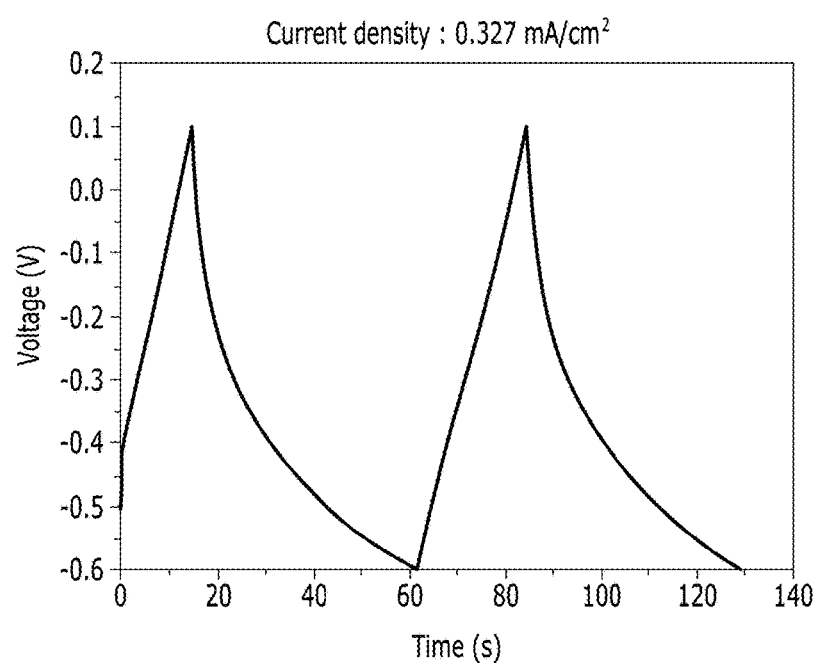
Figure 15B:
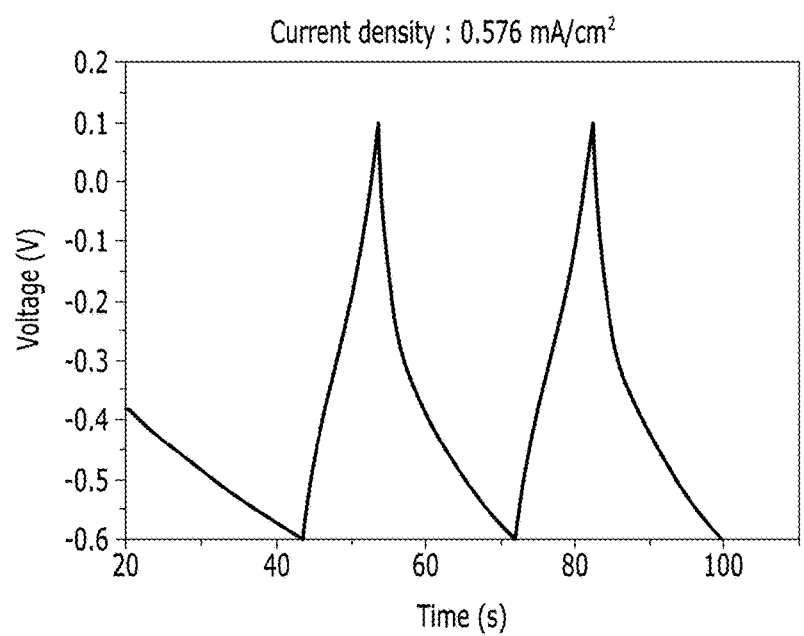
Figure 16B:
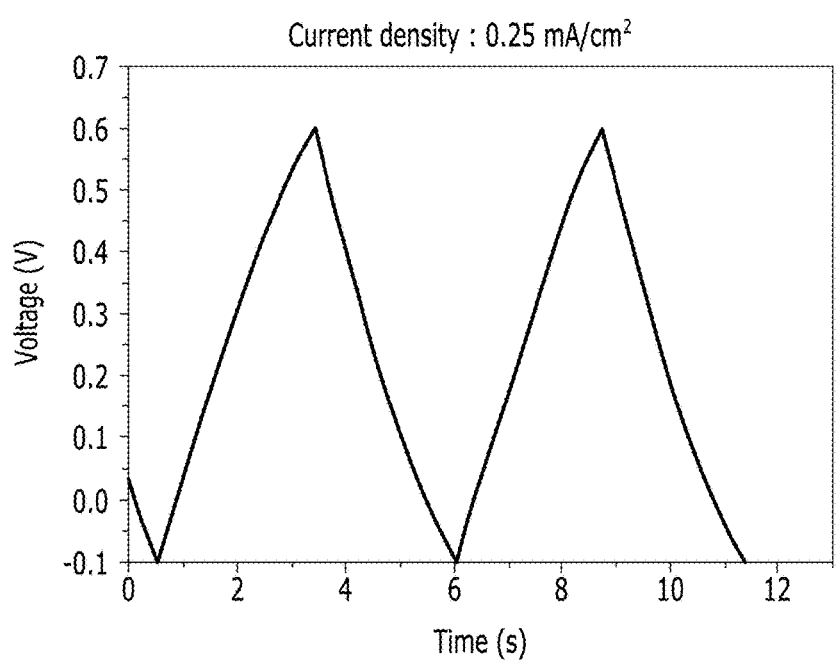
Figure 17B:
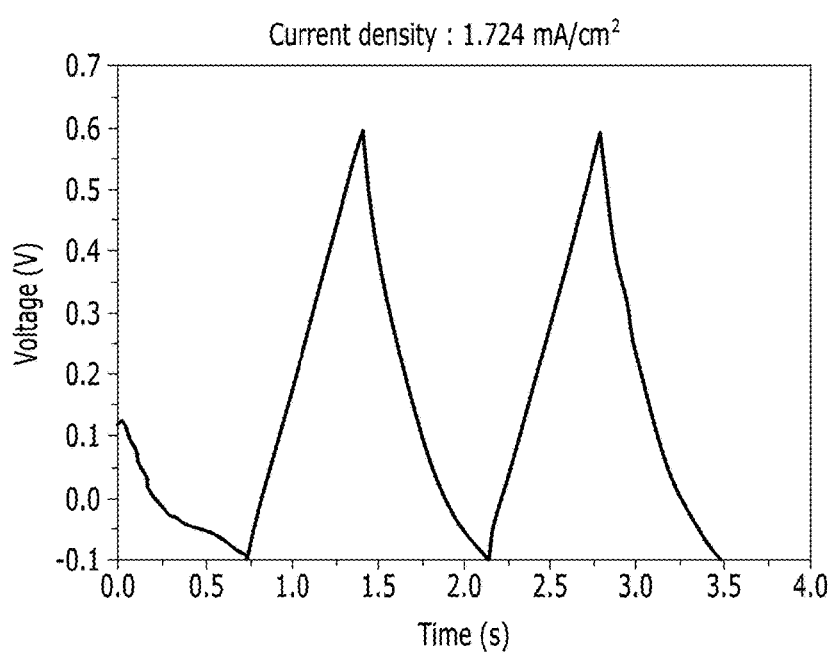
Figure 18B:
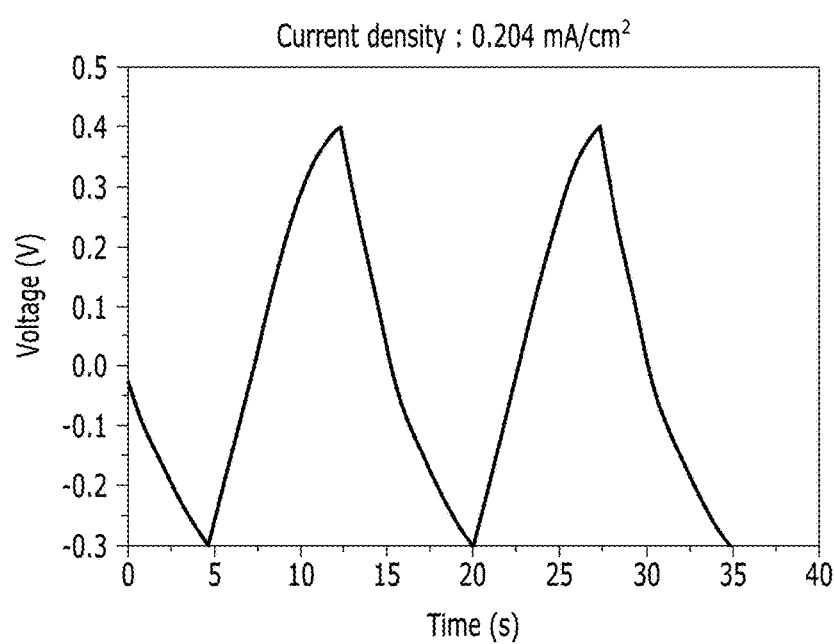
Figure 19B:
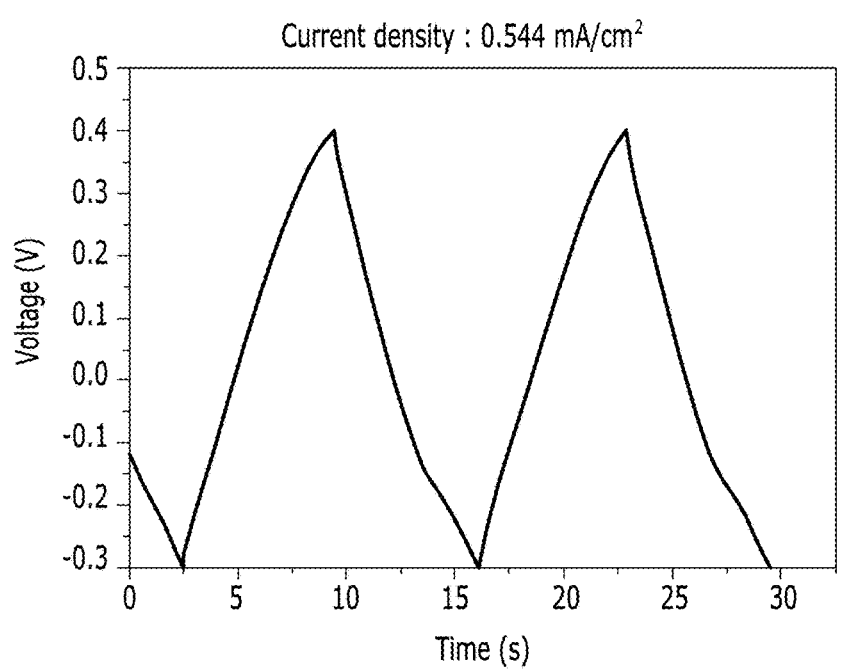

In addition, FIG. 10B (Example 1), FIG. 11B (Comparative Example 1), FIG. 12B (Example 2), FIG. 13B (Comparative Example 2), FIG. 14B (Example 3), FIG. 15B (Comparative Example 3), FIG. 16B (Example 4), FIG. 17B (Comparative Example 4), FIG. 18B (Example 5), and FIG. 19B (Comparative Example 5) show a voltage depending time when a predetermined current flows.

Referring to FIGS. 10A to 20, each half-cell including an anthracene-based polymer according to Examples 1 to 5 showed large specific capacitance and excellent charge and discharge characteristics compared with each half-cell including no anthracene-based polymer according to Comparative Examples 1 to 5.

In particular, an electrolyte solution including chloride ions turned out to have large specific capacitance and excellent charge and discharge efficiency compared with an electrolyte solution including no chloride ions.

DESCRIPTION OF SYMBOLS

10: film
20: current collector
100: electrode

What is claimed is:
1. An electrode comprising
a current collector and a film located on the current collector,
wherein the film includes
an organic semiconductor material and at least one selected from a carbon material, a metal oxide, and a conductive polymer,
wherein the organic semiconductor material is a monomolecular organic photoluminescent material or a polymeric organic photoluminescent material,
wherein the monomolecular organic photoluminescent material includes anthracene or pyrene,
wherein the polymeric organic photoluminescent material includes anthracene-based polymer including a repeating unit represented by Chemical Formula 1:

[Chemical Formula 1]

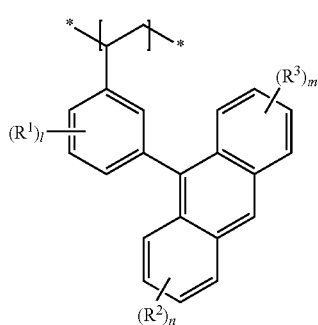

wherein in Chemical Formula 1,
R$^1$ to R$^3$ are independently hydrogen atom, a halogen atom or a substituted or unsubstituted C1 to C10 alkyl group, and
l, n, and m are independently an integer ranging from 0 to 4.

2. The electrode of claim 1, wherein the film includes a carbon material and an organic semiconductor material.

3. The electrode of claim 2, wherein the film further includes a surfactant.

4. The electrode of claim 3, wherein an amount of the carbon material and the surfactant is five times to fifteen times greater than an amount of the organic semiconductor material.

5. The electrode of claim 1, wherein the carbon material is activated carbon, an activated carbon fiber, carbon black, graphite, graphene, graphene oxide, carbon aerogel, carbon zerogel, mesoporous carbon, meso/macroporous carbon, a carbon nanotube, a vapor grown carbon fiber, or a combination thereof.

6. The electrode of claim 5, wherein the carbon material is a carbon nanotube.

7. The electrode of claim 1, wherein the metal oxide is an oxide of a metal including copper, nickel, ruthenium, manganese, molybdenum, vanadium, aluminum, tantalum, gold, silver, iridium, iron, cobalt, chromium, tungsten, titanium, palladium, tin, or a combination thereof.

8. The electrode of claim 1, wherein the conductive polymer includes a a polyaniline-based, polythiophene-based, polypyrrole-based, polyacetylene-based, polyparaphenylene-based polymer, or a combination thereof.

9. The electrode of claim 1, wherein the anthracene-based polymer has a glass transition temperature of 80° C. to 120° C.

10. The electrode of claim 1, wherein the anthracene-based polymer has a thermal decomposition temperature of 250° C. to 300° C.

11. The electrode of claim 1, wherein the anthracene-based polymer has a weight average molecular weight of 1,000 g/mol to 100,000 g/mol.

12. The electrode of claim 1, wherein the current collector is stainless steel.

13. A method of manufacturing an electrode, comprising
mixing at least one selected from a carbon material, a metal oxide, and a conductive polymer, an organic semiconductor material, and a solvent to prepare a mixture;
coating the mixture on a current collector; and
drying the coated mixture on the current collector.
wherein the organic semiconductor material is a monomolecular organic photoluminescent material or a polymeric organic photoluminescent material,
wherein the monomolecular organic photoluminescent material includes anthracene or pyrene,
wherein the polymeric organic photoluminescent material includes anthracene-based polymer including a repeating unit represented by Chemical Formula 1:

[Chemical Formula 1]

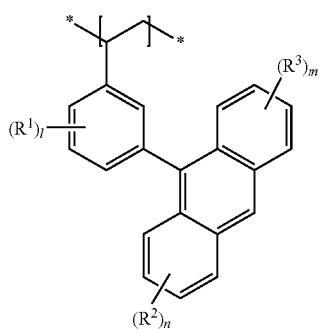

wherein in Chemical Formula 1,
$R^1$ to $R^3$ are independently hydrogen atom, a halogen atom or a substituted or unsubstituted C1 to C10 alkyl group, and
l, n, and m are independently an integer ranging from 0 to 4.

14. The method of manufacturing the electrode of claim 13, wherein the preparing of the mixture is mixing of the carbon material, the organic semiconductor material, and the solvent to prepare a mixture.

15. The method of manufacturing the electrode of claim 13, wherein the carbon material is activated carbon, an activated carbon fiber, carbon black, graphite, graphene, graphene oxide, carbon aerogel, carbon zerogel, mesoporous carbon, meso/macroporous carbon, a carbon nanotube, a vapor grown carbon fiber, or a combination thereof.

16. The method of manufacturing the electrode of claim 15, wherein the carbon material is a carbon nanotube.

17. The method of manufacturing the electrode of claim 13, wherein the metal oxide is an oxide of a metal including copper, nickel, ruthenium, manganese, molybdenum, vanadium, aluminum, tantalum, gold, silver, iridium, iron, cobalt, chromium, tungsten, titanium, palladium, tin, or a combination thereof.

18. The method of manufacturing the electrode of claim 13, wherein the conductive polymer includes a polyaniline-based, polythiophene-based, polypyrrole- based, polyacetylene-based, polyparaphenylene-based polymer, or a combination thereof.

19. The method of manufacturing the electrode of claim 13, wherein the anthracene-based polymer has a glass transition temperature of 80° C. to 120° C.

20. The method of manufacturing the electrode of claim 13, wherein the anthracene-based polymer has a thermal decomposition temperature of 250° C. to 300° C.

21. The method of manufacturing the electrode of claim 13, wherein the anthracene-based polymer has a weight average molecular weight of 1,000 g/mol to 100,000 g/mol.

22. The method of manufacturing the electrode of claim 14, wherein the mixture further includes a surfactant.

23. The method of manufacturing the electrode of claim 22, wherein an amount of the carbon material and the surfactant is five times to fifteen times greater than an amount of the organic semiconductor material.

24. The method of manufacturing the electrode of claim 13, wherein the current collector is stainless steel.

25. The method of manufacturing the electrode of claim 13, wherein the coating is blade coating.

26. The method of manufacturing the electrode of claim 13, wherein the drying is performed by heat-treating the coated mixture at 150° C. to 250° C. for 9hours to 15 hours.

27. A supercapacitor comprising an electrode,
wherein the electrode comprising
a current collector and a film located on the current collector,
wherein the film includes
an organic semiconductor material and at least one selected from a carbon material, a metal oxide, and a conductive polymer.
wherein the organic semiconductor material is a monomolecular organic photoluminescent material or a polymeric organic photoluminescent material,
wherein the monomolecular organic photoluminescent material includes anthracene or pyrene,
wherein the polymeric organic photoluminescent material includes anthracene-based polymer including a repeating unit represented by Chemical Formula 1:

[Chemical Formula 1]

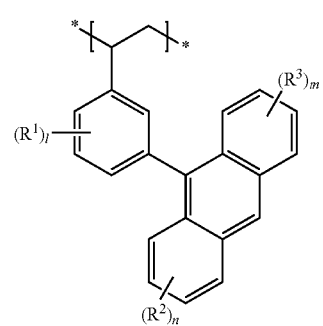

wherein in Chemical Formula 1,
$R^1$ to $R^3$ are independently a hydrogen atom, a halogen atom or a substituted or unsubstituted C1 to C10 alkyl group, and
l, n, and m are independently an integer ranging from 0 to 4.

28. The supercapacitor of claim 27, wherein the supercapacitor further includes an electrolyte solution and a separator.

29. The supercapacitor of claim 28, wherein the electrolyte solution includes a chloride ion.

* * * * *